(12) United States Patent
Talish

(10) Patent No.: US 6,503,214 B1
(45) Date of Patent: Jan. 7, 2003

(54) CAST PUNCH

(75) Inventor: Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/435,123

(22) Filed: Nov. 4, 1999

Related U.S. Application Data

(63) Continuation of application No. PCT/US97/16341, filed on Sep. 16, 1997.
(60) Provisional application No. 60/026,391, filed on Sep. 16, 1996.

(51) Int. Cl.[7] .................................................. A61F 5/00
(52) U.S. Cl. .......................... 602/9; 606/105.5; 606/184
(58) Field of Search .................... 602/9, 6, 14; 606/171, 606/172, 105.5, 167, 184, 174, 185; 128/754; 30/113.1, 316; 83/188, 191, 179, 111, 207; 408/96–98; 623/10; 227/179.1, 180.1

(56) References Cited

U.S. PATENT DOCUMENTS

| | | | |
|---|---|---|---|
| 2,704,067 A | * 3/1955 | Moses ........................... | 602/14 |
| 3,701,352 A | * 10/1972 | Bosworth .................... | 606/184 |
| 4,502,491 A | 3/1985 | Ender et al. | |
| 4,530,360 A | 7/1985 | Duarte | |
| 4,535,779 A | 8/1985 | Ober et al. | |
| 4,574,809 A | 3/1986 | Talish et al. | |
| 4,583,550 A | 4/1986 | Montalbano et al. | |
| 4,898,160 A | * 2/1990 | Brownlee .................... | 602/14 |
| 4,957,499 A | * 9/1990 | Lipatov et al. .......... | 227/180.1 |
| 5,003,965 A | 4/1991 | Talish et al. | |
| 5,186,162 A | 2/1993 | Talish et al. | |
| 5,211,160 A | 5/1993 | Talish et al. | |
| 5,556,372 A | 9/1996 | Talish et al. | |

* cited by examiner

Primary Examiner—Kennedy Schaetzle
Assistant Examiner—Kristen Droesch
(74) Attorney, Agent, or Firm—Kristin L. Johnson; Bruce D. Gray; Kilpatrick Stockton LLP

(57) ABSTRACT

A cast punch and mounting assembly for forming an opening in an orthopedic cast and securing a therapeutic treatment device within the opening adjacent a bone or musculoskeletal injury is provided. The assembly includes a cast punch housing which is fastened to the body surface beneath the cast. The cast punch housing includes a central bore and a guide rod extending outwardly from the central bore. The guide rod extends through the cast. A punch member and a drive member are operably connected to the guide rod and are moveable towards the central bore of the cast punch housing to core an opening in the cast above the central bore. The central bore includes engagement structure to releasably secure a therapeutic treatment device within the central bore of the cast punch housing.

19 Claims, 9 Drawing Sheets

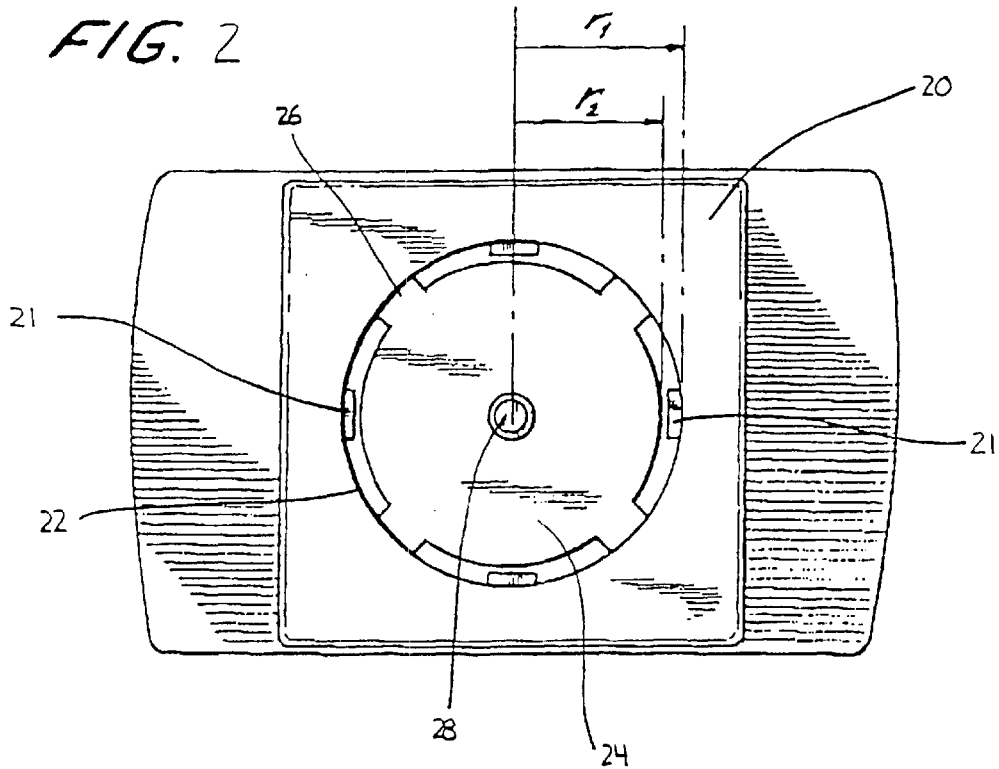
FIG. 2
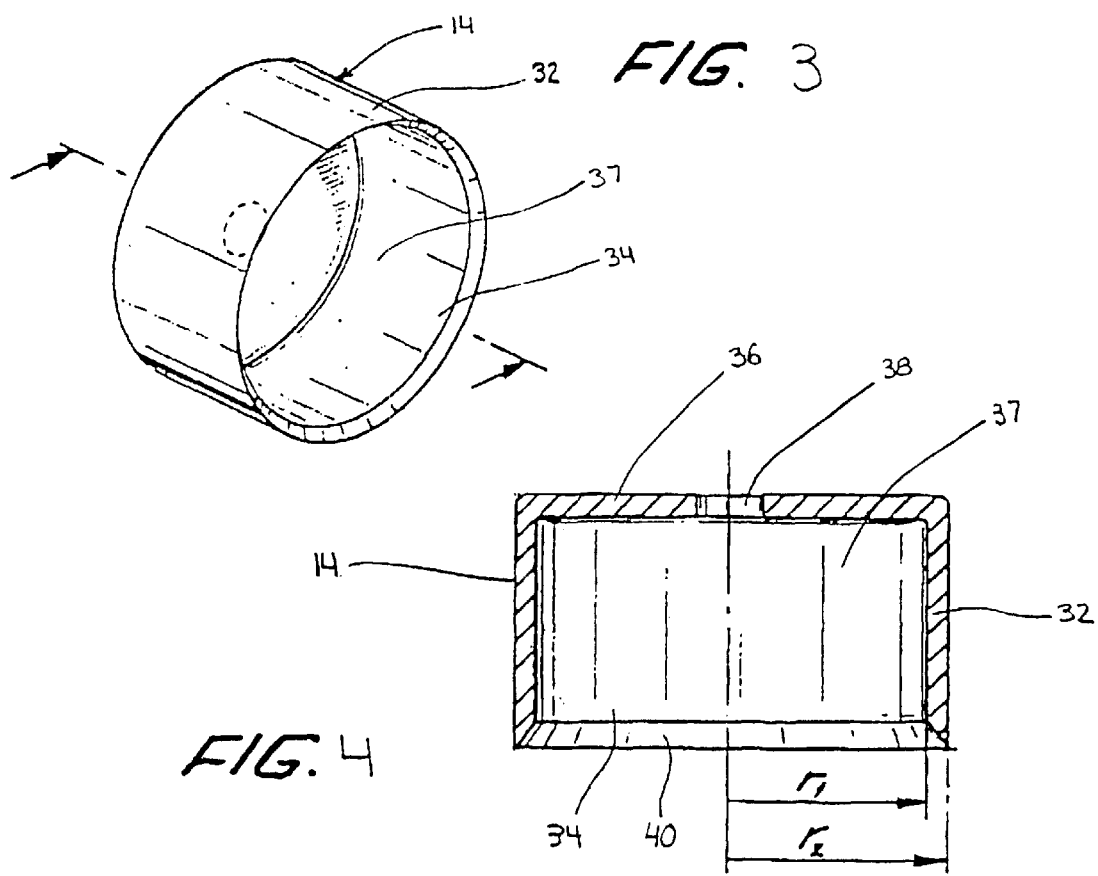
FIG. 3
FIG. 4

CAST PUNCH

This application is a continuation of PCT/US 97/16341 filed Sep. 16, 1997 and claims the benefit of provisional application Ser. No. 60/026,391 filed Sep. 16, 1996.

BACKGROUND OF THE INVENTION

1. Field of the Invention

The present disclosure relates to a cast punch and mounting assembly for a therapeutic treatment device. More specifically, the present disclosure relates to a cast punch and mounting assembly that provides a precisely positioned opening in an orthopedic cast and securely fastens a therapeutic treatment device within the opening at an external location adjacent a musculoskeletal injury.

2. Description of the Related Art

The use of ultrasound to therapeutically treat and evaluate bone injuries is known. Impinging ultrasonic pulses having appropriate parameters, e.g., frequency, pulse, repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

Typically, an ultrasonic delivery system includes an ultrasonic unit having a transducer and a mounting assembly for mounting an operative surface of the transducer against the skin at a fixed position externally of a musculoskeletal or bone injury. Positioning the operative surface of the transducer at the approximate external skin location of the injury optimizes the ultrasonic therapy. If the operative surface of the transducer is not correctly located, the ultrasound received at the injury may be attenuated, resulting in less than ideal healing time of the bone injury.

One problem associated with ultrasonic delivery systems is accurately positioning the transducer of the ultrasonic delivery system with respect to a bone injury when the system is used to promote healing of a bone injury set in a cast. U.S. Pat. No. 4,530,360 to Duarte ("Duarte") describes a basic therapeutic device for applying ultrasonic pulses from an operative surface of a transducer placed on the skin to a bone injury. Duarte states that the device may be used in conjunction with a cast by providing a window in the cast directly above the fracture site. U.S. Pat. No. 5,003,965 to Talish et al. ("Talish") also describes a therapeutic device having a transducer for applying ultrasonic pulses to a bone injury. Talish suggests incorporating a fixture into the stockinette of a cast prior to applying plaster to the cast. The fixture includes engagement structure to secure the transducer with respect to the cast. However, movement of the stockinette during placement about the bone injury and during application of the plaster about the stockinette may result in inaccurate placement of the fixture and thus inaccurate placement of the transducer with respect to the bone injury.

Accordingly, a need exists for an improved assembly for accurately mounting and positioning a therapeutic treatment device onto a cast that overcomes the above-noted disadvantages, is easy to use, and provides better results in healing musculoskeletal and bone injuries.

SUMMARY OF THE INVENTION

In accordance with the present disclosure, a cast punch and mounting assembly is provided that is capable of accurately coring an opening in a cast and securing a therapeutic treatment device in the opening. The cast punch and mounting assembly includes a cast punch housing having a central bore, a punch member movable towards the central bore, and a drive member operably engaged with the punch member and movable to advance the punch member towards the central bore of the housing. The punch member may include an annular cutting edge that is advanced by the drive member to provide the opening in the cast. A guide member including a threaded guide rod may be provided to align the punch member with the central bore of the housing and to operably engage the drive member.

BRIEF DESCRIPTION OF THE DRAWINGS

Various preferred embodiments are described herein with reference to the drawings, wherein:

FIG. 2 is a top view of the cast punch housing shown in FIG. 1;

FIG. 3 is a perspective view from the bottom of the punch member shown in FIG. 1;

FIG. 4 is a side cross-sectional view of the punch member shown in FIG. 1;

FIG. 14 is a perspective view of the cast punch housing having the guide rod and cover removed and a therapeutic treatment device aligned with the central bore of the cast punch housing;

DETAILED DESCRIPTION OF THE PREFERRED EMBODIMENTS

Figure 1:
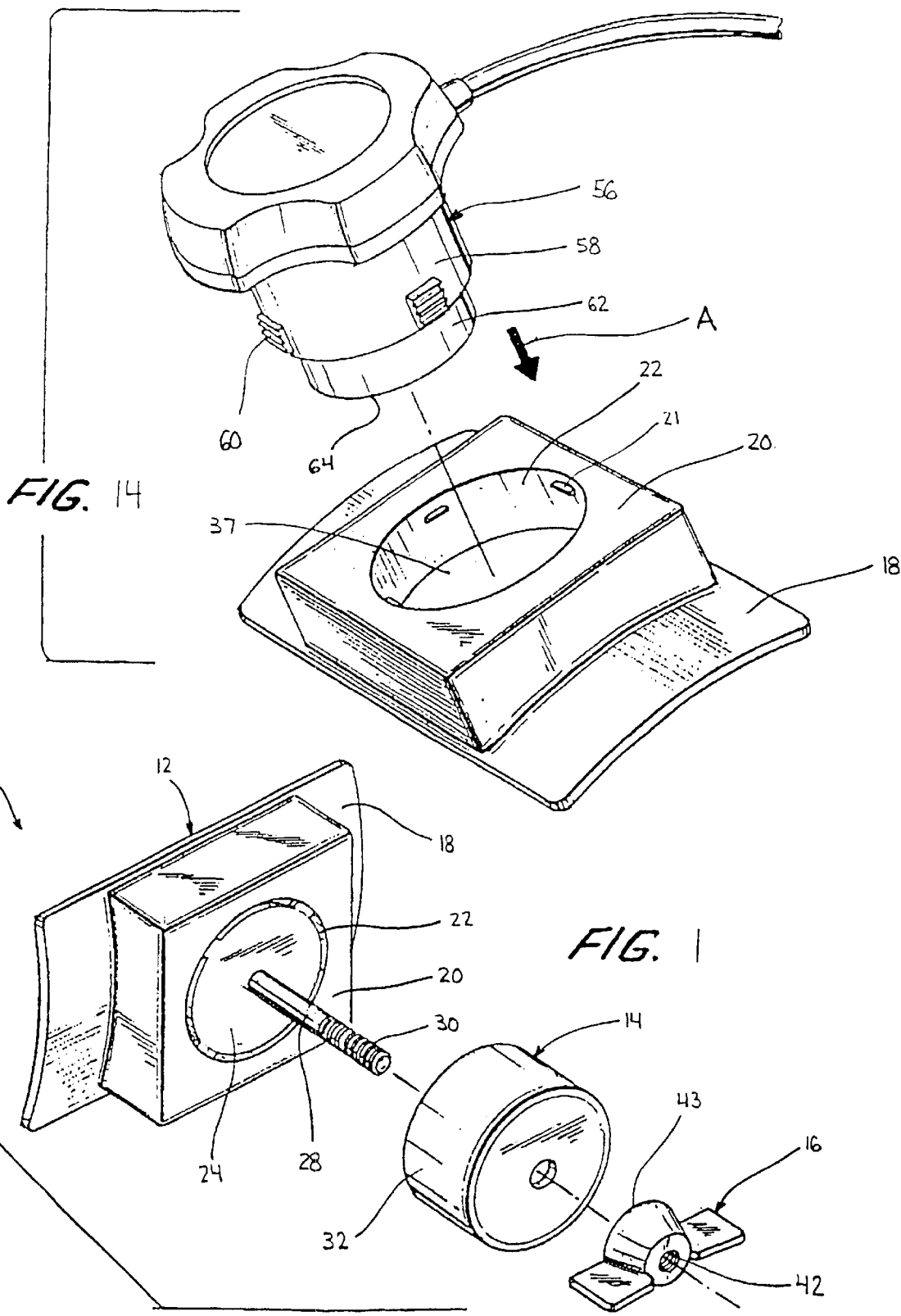
FIG. 1 is a perspective view with parts separated of one embodiment of the cast punch and mounting assembly.

Preferred embodiments of the presently disclosed cast punch and mounting assembly will now be described in detail with reference to the drawings, in which like reference numerals designate identical or corresponding elements in each of the several. views.

One embodiment of the presently disclosed cast punch and mounting assembly will now be described with reference to FIGS. 1–4. FIG. 1 illustrates the cast punch and mounting assembly shown generally as 10. Briefly, cast punch and mounting assembly 10 includes a cast punch housing 12, a punch member 14 and a drive member 16. Cast punch housing 12 includes a base member 18 having an engagement surface configured to be supported on a body surface at a location adjacent an injury, e.g., the arm or the leg. A body portion 20 of housing 12 projects outwardly from the base member 18 and is formed with a central bore 22 having a plurality of bayonet locking lugs 21 formed about its inner periphery. (See FIG. 2)

Referring to FIG. 2, a removable cover 24 having a plurality of breakaway tabs 26 releasably fastened to the inner wall of the central bore 22 covers central bore 22 of body portion 20. A guide rod 28 aligned with the central axis of central bore 22 extends upwardly from the removable cover 24 away from central bore 22. The guide rod 28 may be formed with screw threads 30 which are dimensioned to engage the drive member 16 (See FIG. 1), although other conventional engagement structure may also be used to interconnect the drive member 16 with the guide rod 28, i.e., a ratchet.

FIGS. 3 and 4 illustrate the punch member 14 which includes a cylindrical body 32 having an open end 34 and a top wall 36 defining a punch chamber 37. An opening 38 formed in the top wall 36 is dimensioned to slidably receive guide rod 28. (See FIG. 1) Cylindrical body 32 includes an annular cutting edge 40. The cutting edge 40 may be a flat or serrated surface, but is preferably a bevelled surface. Although punch member 14 is disclosed as having a cylindrical body 32, the punch member 14 may be formed having any desired shape, i.e., square, rectangular, oblong, but should have a shape that corresponds to the shape of the central bore 22.

Figure 4A:
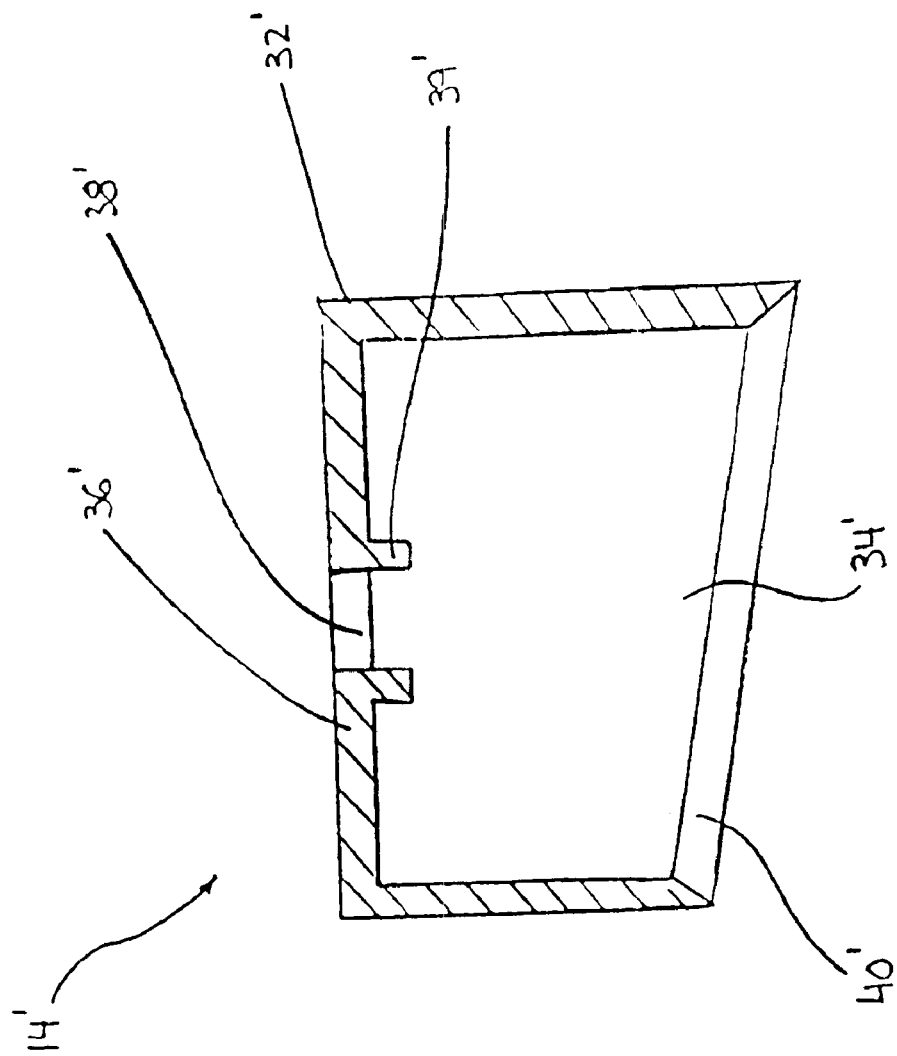
FIG. 4A is a side cross-sectional view of an alternate embodiment of the punch member.

FIG. 4A illustrates an alternate embodiment of the punch member 14 shown generally as 14'. Punch member 14' includes an obliquely truncated cylindrical body 32' having an open end 34', a top wall 36' and an annular cutting edge 40'. An opening 38' formed in top wall 36' is defined by an inwardly extending annular flange 39' dimensioned to receive guide rod 28 (See FIG. 1). The annular flange 39' prevents punch member 14' from canting when the cutting edge 40 engages the cast material.

Referring temporarily back to FIG. 1, the drive member 16 may be a hreaded wing nut having threads that engage the screw threads 30 formed on guide rod 28. Alternately, the drive member may be in the form of any other known drive mechanism, such as a ratchet. As drive member 16 is advanced along guide rod 28 (by rotating wing nut 16 in FIG. 1, for example), a front surface 43 of drive member 16 engages and advances punch member 14 along guide rod 28 towards central bore 22 of cast punch housing 12.

Figure 5:
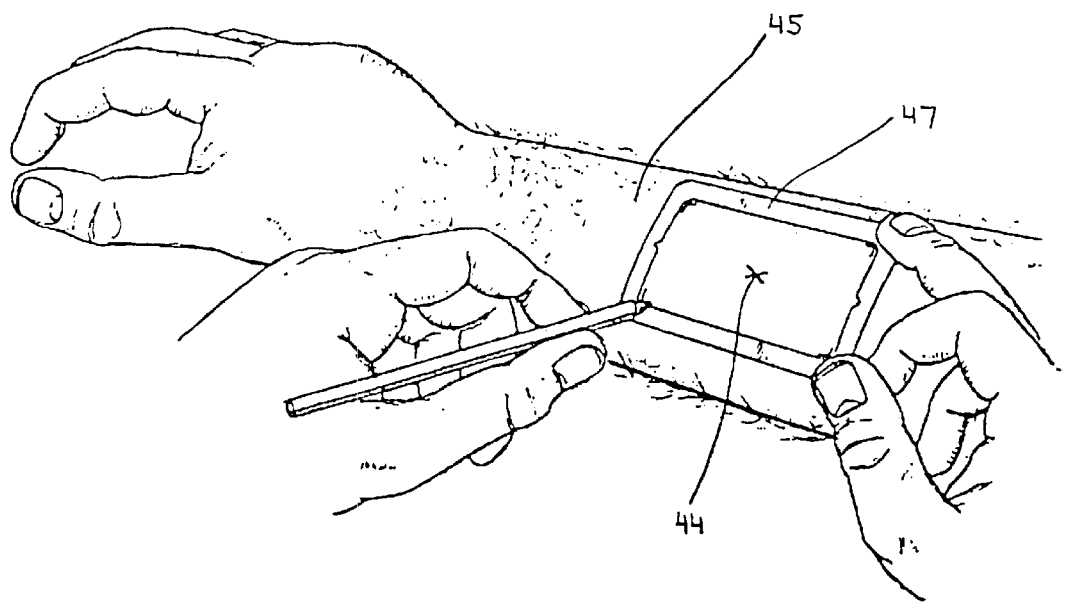
FIG. 5 is a perspective view of a patient's arm having a template positioned to define a predetermined location on the external surface of the arm.
Figure 6:
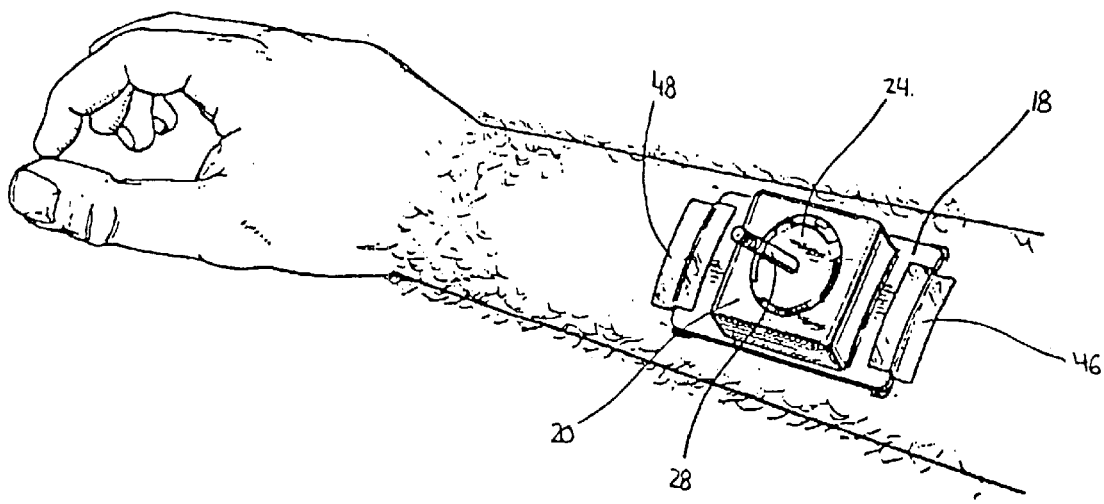
FIG. 6 is a perspective view of the arm shown in FIG. 5 with the cast punch housing shown in FIG. 1 fastened to the predetermined location.

Referring to FIGS. 5–13, placement and operation of the cast punch and mounting assembly 10 will now be described. As shown in FIGS. 5 and 6, a template 47 is positioned about a mark 44 made on the skin 45. The mark 44 identifies the external location of a bone fracture or musculoskeletal injury, and may be determined using the method set forth in U.S. patent application Ser. No. 08/388, 971, filed Feb. 15, 1995, incorporated herein by reference. The template 42 has a shape that corresponds to the base member 18 of the casting punch housing 12. A tracing is made using the template 47 and the cast punch housing 12 is secured on the tracing with adhesive strips 46 and 48.

Figure 7:
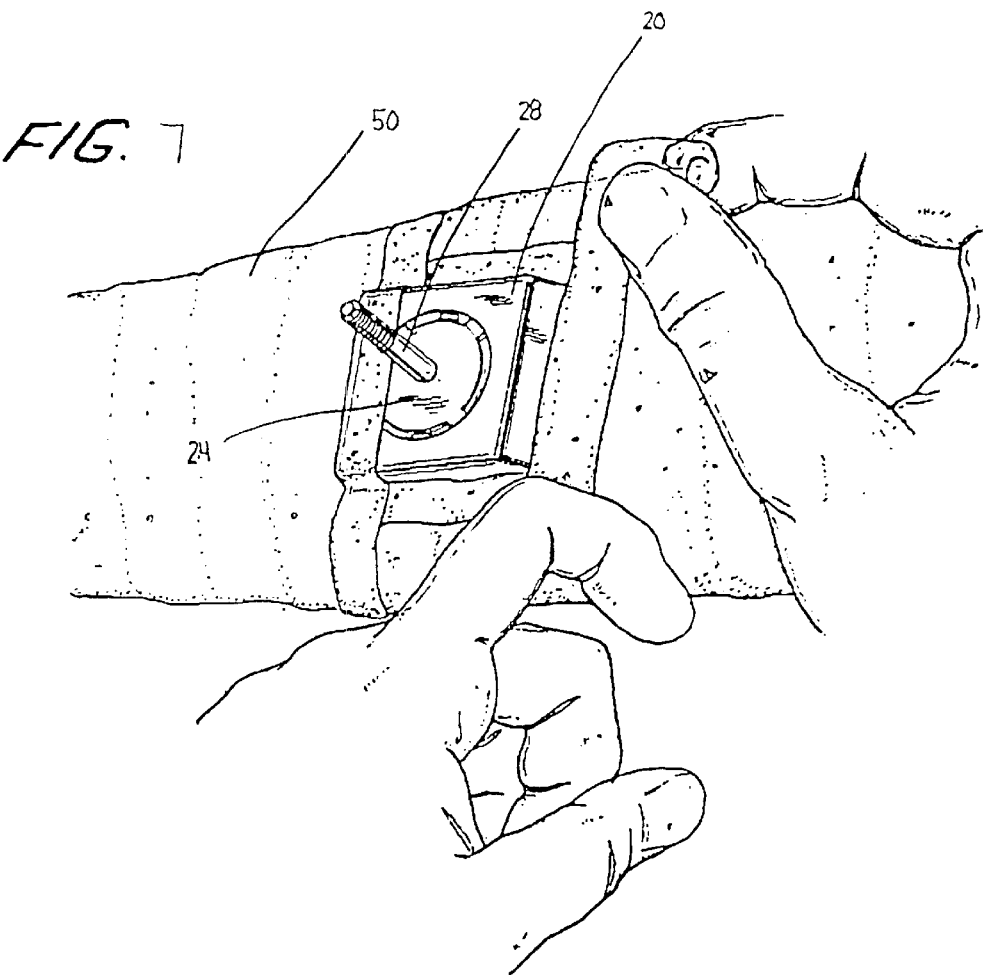
FIG. 7 is a perspective view of the arm and cast punch housing shown in FIG. 6 partially wrapped in an orthopedic cast.
Figure 8:
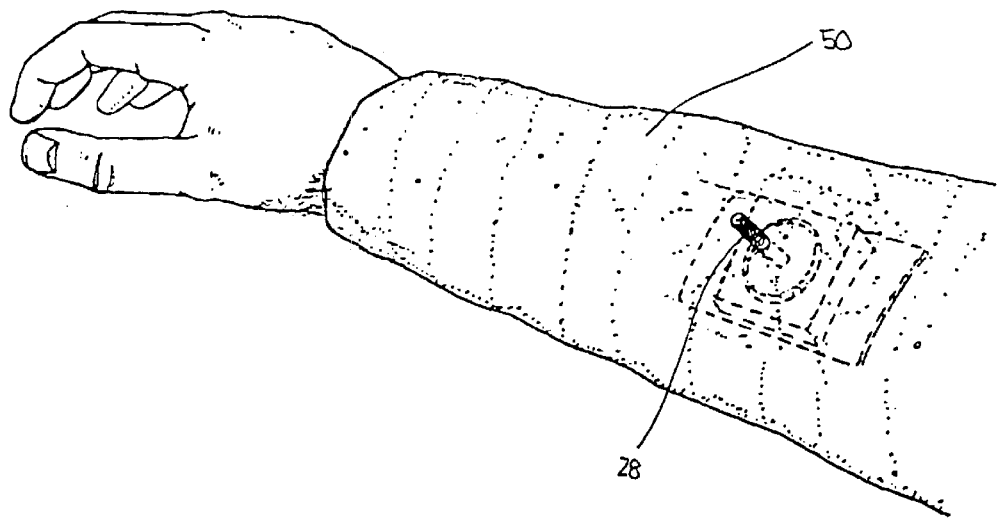
FIG. 8 is a perspective view of the arm and cast punch housing shown in FIG. 6 fully wrapped in an orthopedic cast.
Figure 9:
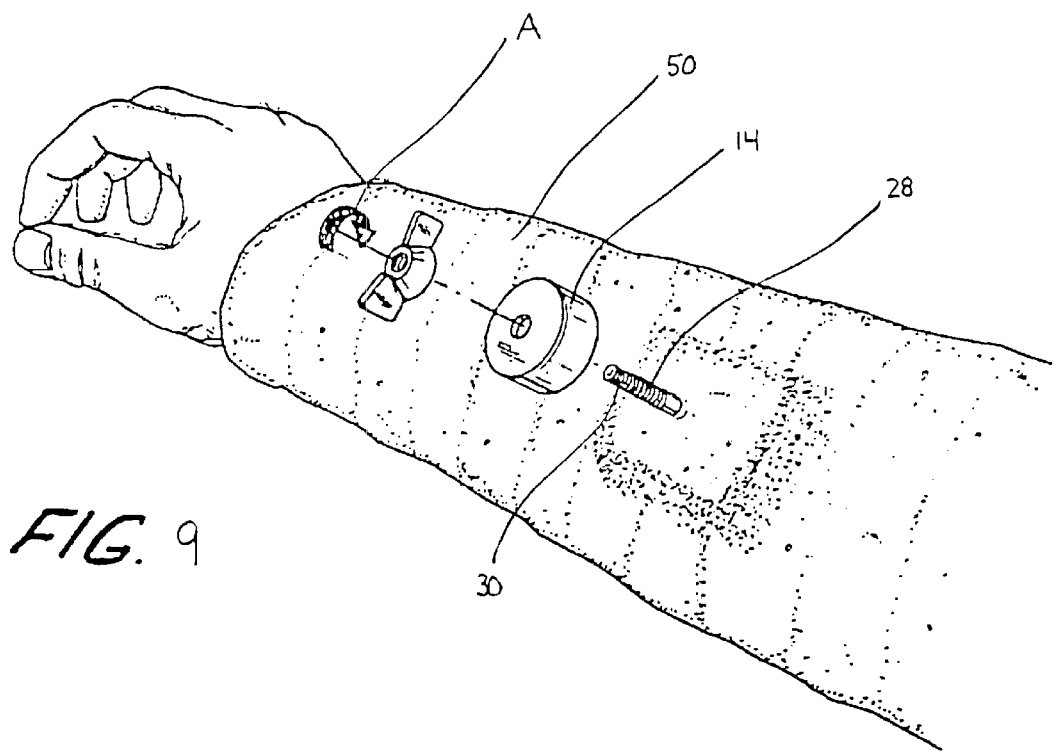
FIG. 9 is a perspective view of the cast punch housing and cast shown in FIG. 8 further including the punch member and drive member shown in FIG. 1 with parts separated.
Figure 10:
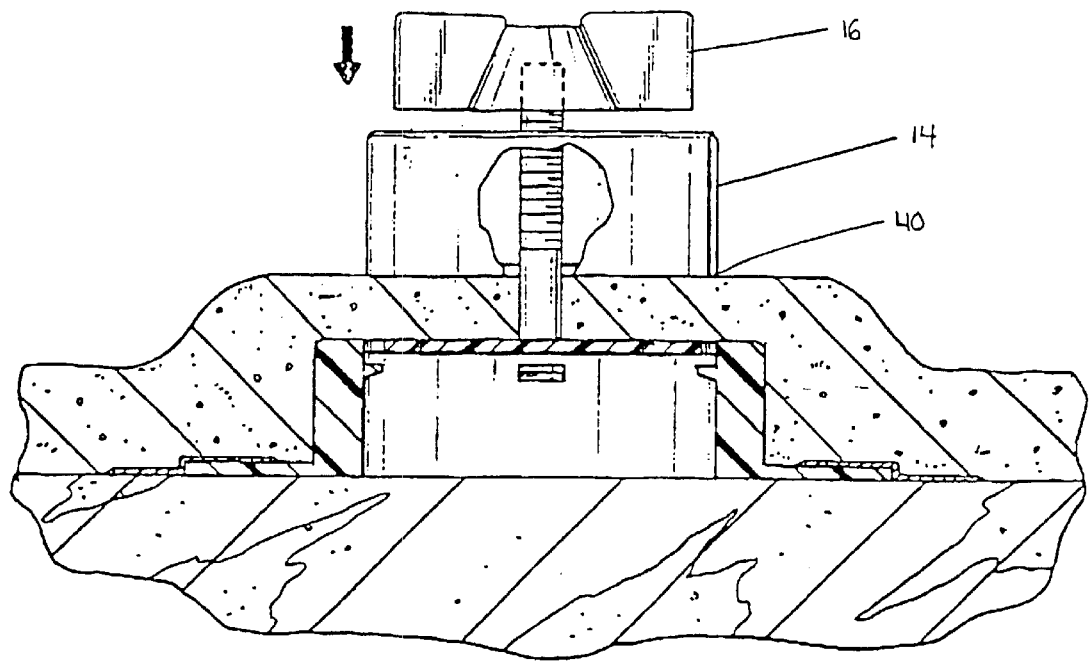
FIG. 10 is a partial side cross-sectional view of the cast punch and mounting assembly and cast shown in FIG. 9 with the drive member spaced from the punch member.
Figure 11:
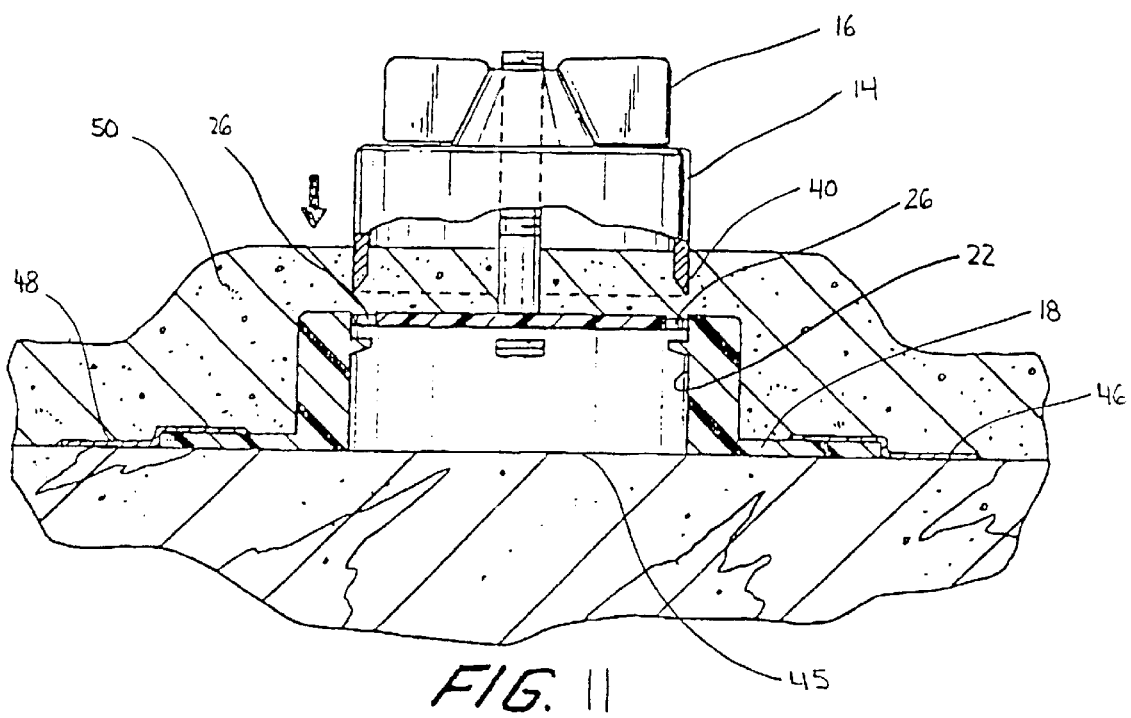
FIG. 11 is a partial side cross-sectional view of the cast punch and mounting assembly and cast shown in FIG. 10 with the drive member engaging the punch member and the punch member extending partially through the cast.
Figure 12:
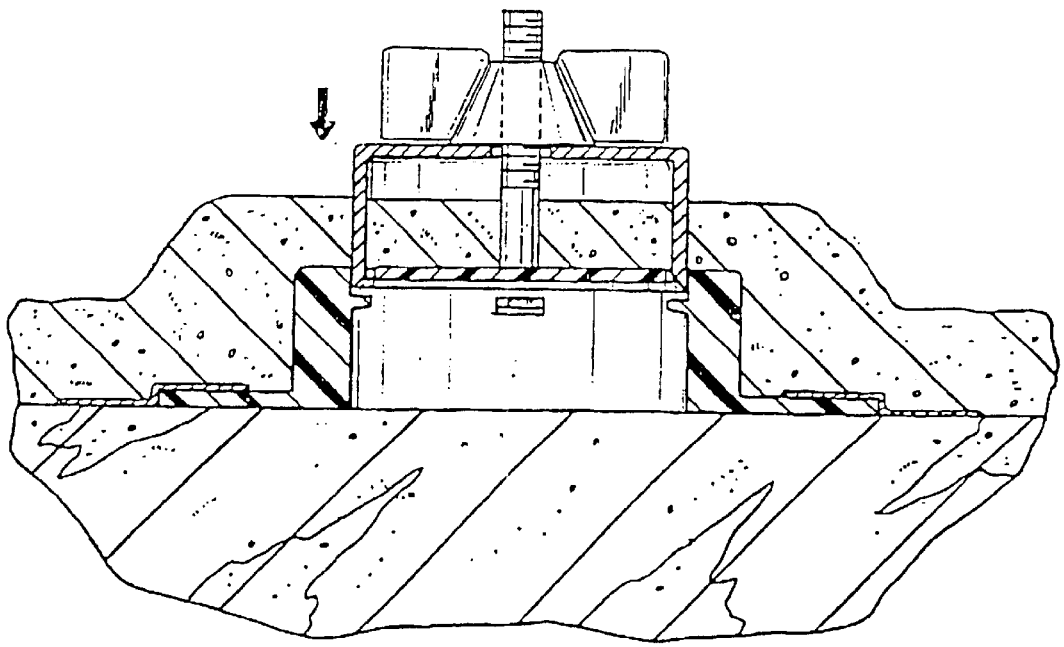
FIG. 12 is a partial side cross-sectional view of the cast punch and mounting assembly and cast shown in FIG. 11 with the punch member extending through the cast.

Referring to FIGS. 7–9, a cast 50 is applied about the location of the body corresponding to the bone fracture or musctiloskeletal injury and about the cast punch housing 12 such that only the guide rod 28 projects through the cast 50. When it is desired to create a hole in the cast 50, the punch member 14 is positioned about the guide rod 28 and the threads of the drive member 16 are engaged with threaded end 30 of the guide rod 28 and the drive members advanced along the guide rod by rotating.

As illustrated in FIGS. 9–12, the drive member 16 is rotated to advance the cutting edge 40 of punch member 14 into engagement with the portion of cast 50 covering the central bore 22 of cast punch housing 12. Continued advancement of drive member 16 forces the cutting edge 40 through cast 50 and into engagement with tabs 26 of cover 24 disengaging tabs 26 from housing 12. The bayonet locking lugs 21 prevent the cutting edge 40 from advancing through the central bore 22 and engaging the skin 45 of a patient.

Figure 13:
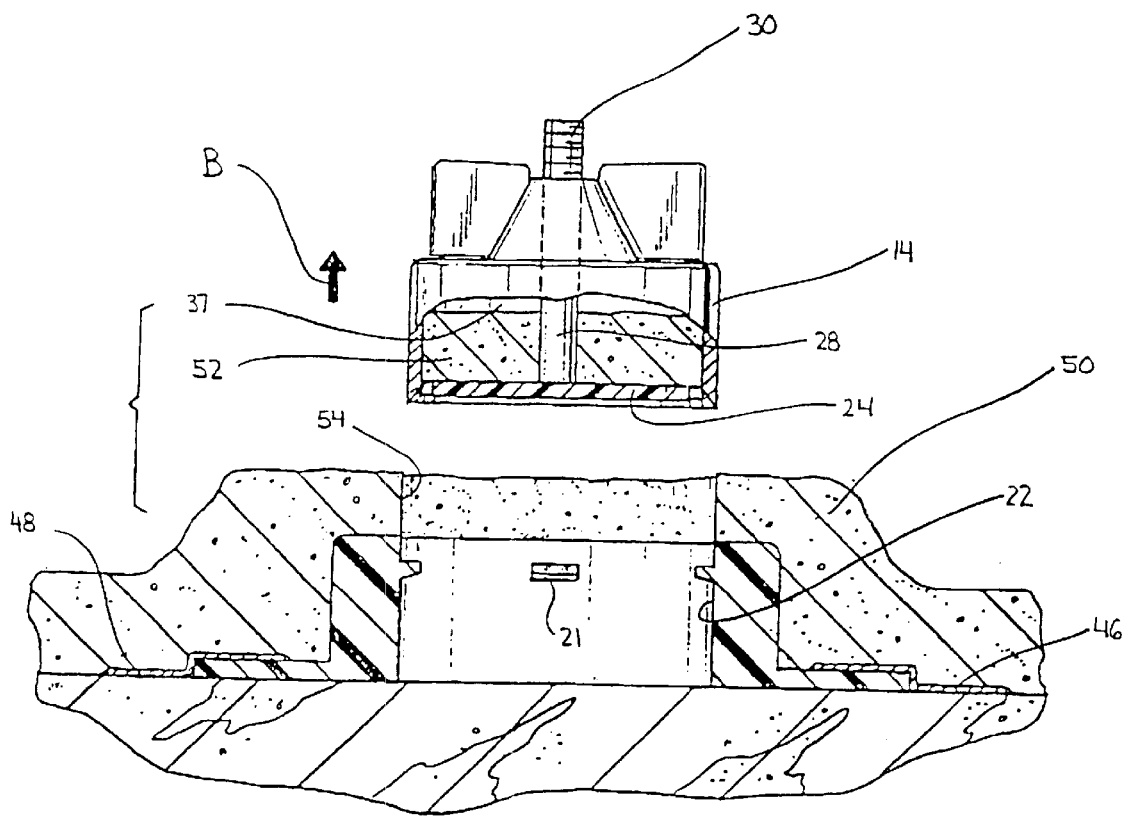
FIG. 13 is a partial side cross-sectional view of the cast punch and mounting assembly and cast shown in FIG. 12 with the cored cast material removed from the opening formed in the cast.

Referring to FIG. 13, the cover 24 which is fastened to the guide rod 28, may be removed from central bore 22 by grasping the threaded end 30 of guide rod 28 or by grasping driving member 16 and pulling the assembly from the central bore 22 in the direction indicated by arrow "B". The cast material 52 cored from cast 50 by punch member 14 is supported on cover 24 within punch chamber 37 and may be removed from cast 50 with cover 24 to provide an opening 54 in the cast 50 for placement of the therapeutic treatment device.

Figure 15:
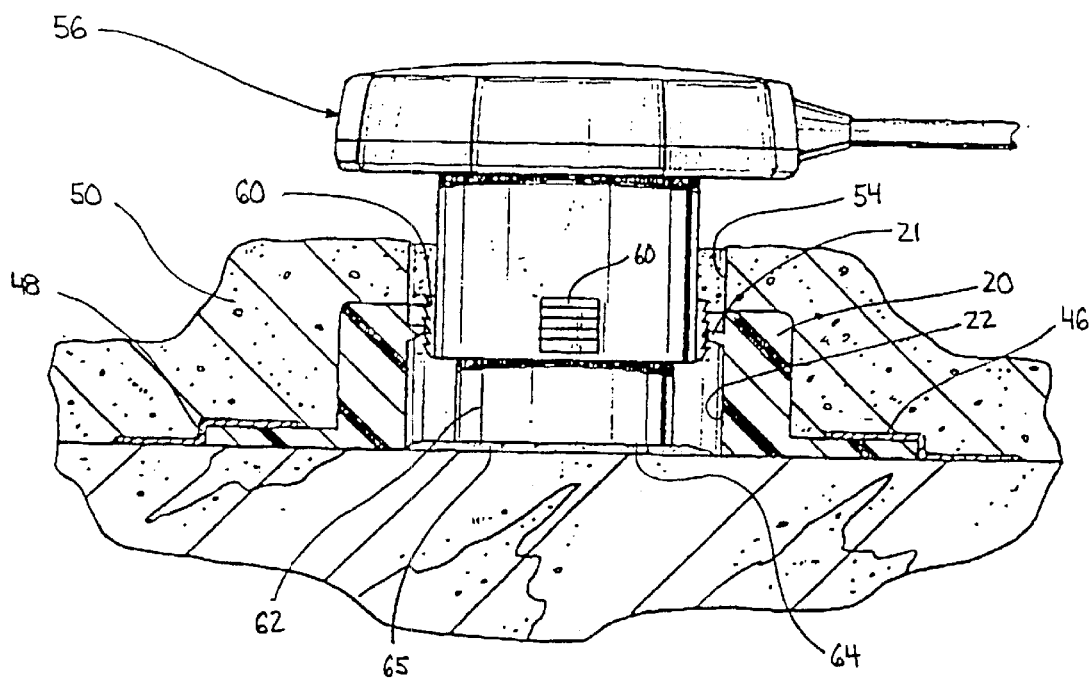
FIG. 15 is a partial side cross-sectional view of the cast mounting assembly with a therapeutic treatment device releasably secured within the central bore of the cast punch housing.

FIGS. 14 and 15 illustrate cast punch housing 12 in association with a therapeutic treatment device 56. The therapeutic treatment device 56 includes a transducer 62 having a shape that corresponds to the shape of the central bore 22 of cast punch housing 12. A plurality of slotted lugs 60 spaced about the periphery of the treatment device 56 are configured to releasably engage bayonet locking lugs 21 extending from the inner periphery of central bore 22. To engage the slotted lugs 60 with bayonet locking lugs 21, transducer 62 is moved in the direction indicated by arrow "A" into central bore 22 of body portion 20. If the locking lugs 21 are vertically aligned with the slotted lugs 60 during insertion of transducer 62 into central bore 22, locking lugs 21 will be deflected into engagement with one of the slots on the lugs 60. If locking lugs 21 are not vertically aligned with the slotted lugs 60 during insertion of transducer 62 into central bore 22, the therapeutic device 56 may be rotated to bring the locking lugs 21 and the slotted lugs 60 into locking engagement to secure the therapeutic treatment device within central bore 22. The transducer 62 should be fixedly positioned with the operative surface 64 adjacent the external location of the bone injury. The operative surface 65 may be coated with a coupling gel 65 before being inserted into the central bore 22 to optimize the ultrasonic therapy. Alternately, a gel bladder may be positioned between the body to be treated and the operative surface of the transducer 62.

Figure 16:
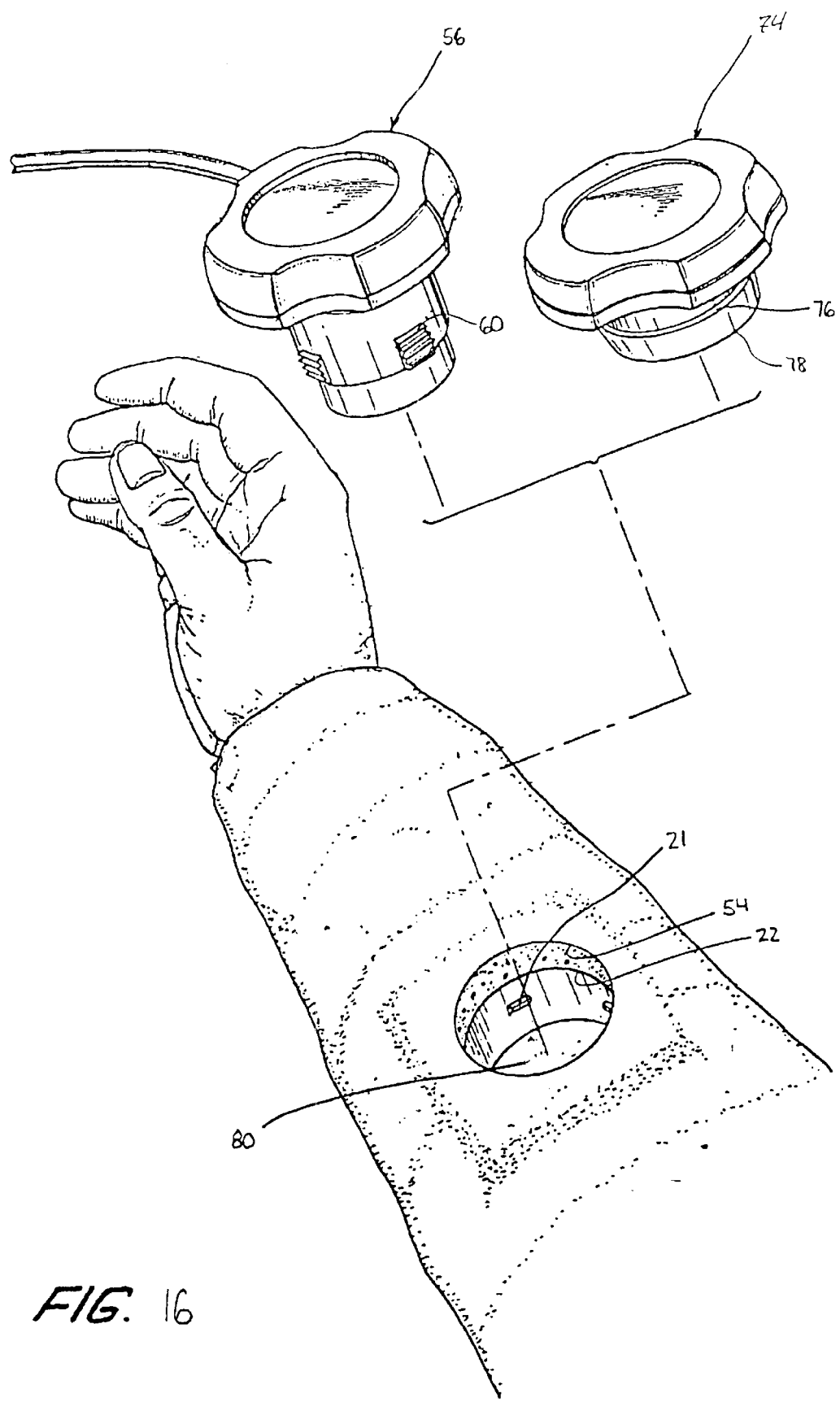
FIG. 16 is a perspective view of the cast punch housing and cast shown in FIG. 15 having an opening with a therapeutic treatment device and a cap aligned for insertion into the opening.

Referring now to FIG. 16, a cap 74 is provided to cover the opening 54 in the cast 50 when the therapeutic treatment device 56 is not in use. The cap 74 may have slotted lugs similar to those provided on the therapeutic treatment device 56 to secure the cap 74 within central bore 22. Alternately, the cap 74 may have an annular stepped portion 76 that engages locking lugs 21 to secure the cap 74 within the central bore 22. The cap 74 includes a contact face 78 which maintains pressure on the skin surface 80 when the device 56 is not in use to prevent "window edemas".

It will be understood that various modifications can be made to the various embodiments of the present disclosure without departing from its spirit and scope. For example, various sizes and shapes of the cast punch and mounting assembly are contemplated, as well as various types of construction materials. Also, an integral punch and drive member is contemplated wherein the punch rotates with the drive member as it cores the opening in the cast. Various types of drive mechanisms to advance the punch through the cast are also contemplated. Therefore, the above description should not be construed as limiting the invention but merely as presenting preferred embodiments of the invention. Those skilled in the art will envision other modifications within the scope and spirit of the disclosure as defined by the claims presented below.

What is claimed is:

1. An apparatus comprising:
   a housing having a bore;
   a punch member having a cutting edge and being movable relative to the bore from the first position spaced from the bore to a second position within the bore;
   a guide member operably associated with the punch member and the housing to restrict movement of the punch member to movement between the first and the second positions; and
   a drive member movable into operable engagement with the punch member to advance the punch member from the first position to the second position,
   wherein the guide member includes a guide rod extending along the central longitudinal axis of the bore and fastened to the housing and wherein the punch member has a central opening configured to slidably engage the guide rod, the punch member being slidable along the guide rod between the first and second positions, and wherein the guide rod has a threaded portion and the drive member has a threaded opening dimensioned to engage the threaded portion of the guide rod, the drive member being rotatable about the guide rod to advance the drive member along the guide rod into engagement with the punch member to advance the punch member from the first position to the second position.

2. An apparatus for providing an opening in a medical wrapping comprising:
   a. a medical wrapping;
   b. a housing having a bore, wherein the bore is at least partially covered by a portion of the medical wrapping;
   c. a punch member having a cutting edge and being movable relative to the bore from a first position spaced from the bore to a second position within the bore so that the cutting edge severs the portion from a remainder of the medical wrapping; and
   d. a guide member operably associated with the punch member and the housing to guide movement of the punch member between the first and second positions.

3. The apparatus of claim 2, further comprising a drive member movable into operable engagement with the punch member to advance the punch member from the first position to the second position.

4. The apparatus of claim 2, wherein the guide member comprises a guide rod extending along the central longitudinal axis of the bore and operatively connected to the housing, wherein the punch member comprises a central opening configured to slidably engage the guide rod so that the punch member is slidable along the guide rod between the first and second positions.

5. The apparatus of claim 4, further comprising a drive member, wherein the drive member engages the guide rod to advance the punch member from the first position to the second position.

6. The apparatus of claim 2, wherein the housing comprises a base member for engaging a body surface.

7. The apparatus of claim 6, wherein the housing further comprises a body portion having the bore.

8. The apparatus of claim 7, wherein the base member and the body portion are integrally-formed.

9. The apparatus of claim 2, further comprising a cover for at least partially covering the bore.

10. The apparatus of claim 2, wherein the punch member comprises a punch body, an open end, and a top wall.

11. The apparatus of claim 10, wherein the punch body is cylindrical.

12. The apparatus of claim 10, wherein the top wall comprises an opening for receiving the guide member.

13. A system for healing a wound, including a bone or musculoskeletal injury, comprising:
   a. a medical wrapping;
   b. an apparatus for providing an opening in the medical wrapping comprising:
      i. a housing having a bore;
      ii. a punch member having a cutting edge and being movable relative to the bore from a first position spaced from the bore to a second position within the bore to form an opening in the medical wrapping; and
      iii. a guide member operably associated with the punch member and the housing to restrict movement of the punch member to movement between the first and the second positions; and
   c. a therapeutic treatment device.

14. The system of claim 13, wherein the therapeutic treatment device comprises a transducer.

15. The system of claim 13, further comprising a cap to cover the opening when the therapeutic treatment device is not in use.

16. A method of providing an opening in a medical wrapping, comprising:
   providing a punch assembly including a housing having a bore and a punch member having a cutting edge, the punch member being movable into the bore;
   positioning the punch assembly housing on a body surface to be medically wrapped;
   applying medical wrapping about the body surface and the punch assembly housing;
   advancing the punch member towards the bore of the housing to drive the cutting edge of the punch member through the medical wrapping to sever at least a portion of the medical wrapping covering the bore; and
   removing the severed portion of the medical wrapping from the bore.

17. A method for healing a wound, including a bone or musculoskeletal injury, comprising:
   a. providing an opening in a medical wrapping by:
      i. providing a punch assembly including a housing having a bore and a punch member having a cutting edge, the punch member being movable into the bore;

ii. positioning the punch assembly housing on a body surface to be medically wrapped;

iii. applying medical wrapping about the body surface and the punch assembly housing;

iv. advancing the punch member towards the bore of the housing to drive the cutting edge of the punch member through the medical wrapping to sever at least a portion of the medical wrapping covering the bore; and v. removing the severed portion of the medical wrapping from the bore to create an opening in the medical wrapping; and b. placing a therapeutic treatment device in the opening and activating the treatment device.

18. The method of claim 17, further comprising removing the therapeutic treatment device from the opening and covering the opening with a cap.

19. The method of claim 17, wherein the therapeutic treatment device comprises a transducer.

* * * * *